(12) United States Patent
Yates et al.

(10) Patent No.: US 8,461,118 B2
(45) Date of Patent: Jun. 11, 2013

(54) LYTIC PEPTIDES HAVING ANTI-PROLIFERATIVE ACTIVITY AGAINST PROSTATE CANCER CELLS

(75) Inventors: Clayton Yates, Auburn, AL (US); Jesse Jaynes, Auburn, AL (US); Timothy Turner, Auburn, AL (US)

(73) Assignee: Tuskegee University, Tuskegge, AL (US)

( * ) Notice: Subject to any disclaimer, the term of this patent is extended or adjusted under 35 U.S.C. 154(b) by 0 days.

(21) Appl. No.: 13/178,042

(22) Filed: Jul. 7, 2011

(65) Prior Publication Data

US 2013/0012437 A1    Jan. 10, 2013

(51) Int. Cl.
*A61K 38/00* (2006.01)
*A61K 38/09* (2006.01)
*A61K 38/16* (2006.01)
*A61K 38/24* (2006.01)

(52) U.S. Cl.
USPC ........ 514/19.5; 514/10.3; 514/21.3; 530/313; 530/324

(58) Field of Classification Search
None
See application file for complete search history.

(56) References Cited

U.S. PATENT DOCUMENTS

| | | | | |
|---|---|---|---|---|
| 5,561,107 A | * | 10/1996 | Jaynes et al. | 514/2.3 |
| 6,635,740 B1 | * | 10/2003 | Enright et al. | 530/324 |
| 8,318,899 B2 | * | 11/2012 | Leuschner et al. | 530/350 |
| 2003/0083243 A1 | * | 5/2003 | Owen | 514/12 |

FOREIGN PATENT DOCUMENTS

WO    WO9012866    * 11/1990

OTHER PUBLICATIONS

Yates et al. 2011. Biochem Pharm. 81:104-110.*

* cited by examiner

*Primary Examiner* — Shulamith H Shafer
(74) *Attorney, Agent, or Firm* — Hogan Lovells US LLP

(57) ABSTRACT

Lytic peptides, including fusion peptides of lytic peptides conjugated with luteinizing hormone-releasing hormone or modified versions thereof to target luteinizing hormone-releasing hormone receptors, are disclosed. The lytic peptides show anti-proliferative activity against human prostate cancer cell lines, but are nontoxic to normal primary human prostate epithelial cells or to bone marrow stromal cells in co-culture. The lytic peptides have specificity for and anti-proliferative activity against prostate cancer tumor cells, and low toxicity for normal prostate cells, making the peptides useful in therapies for prostate cancer.

10 Claims, 12 Drawing Sheets
(5 of 12 Drawing Sheet(s) Filed in Color)

| Cell line | Peptides | | | |
|---|---|---|---|---|
| | JC21 | JCH | JC21mLHRH | JCHmLHRH |
| LNCaP | n.d | n.d | 9.149μM | 4.362μM |
| DU-145 | n.d | n.d | 5.66μM | 4.81μM |
| PC-3 | 9.25μM | 6.67μM | 7.42μM | 4.22μM |

SEQUENCE LISTING

<160> NUMBER OF SEQ ID NOS: 8

<210> SEQ ID NO 1
<211> LENGTH: 23
<212> TYPE: PRT
<213> ORGANISM: Homo sapiens
<220> FEATURE:
<223> OTHER INFORMATION: JCH

<400> SEQUENCE: 1

Phe Ala Leu Ala Leu Lys Ala Leu Lys Lys Ala Leu Lys Lys Leu Lys
1               5                   10                  15

Lys Ala Leu Lys Lys Ala Leu
            20

<210> SEQ ID NO 2
<211> LENGTH: 23
<212> TYPE: PRT
<213> ORGANISM: Homo sapiens
<220> FEATURE:
<223> OTHER INFORMATION: JC21

<400> SEQUENCE: 2

Ala Phe Lys Lys Ala Phe Lys Lys Ala Lys Lys Ala Phe Lys Lys Ala
1               5                   10                  15

Phe Lys Ala Phe Ala Phe Ala
            20

<210> SEQ ID NO 3
<211> LENGTH: 10
<212> TYPE: PRT
<213> ORGANISM: Homo sapiens
<220> FEATURE:
<223> OTHER INFORMATION: LHRH

<400> SEQUENCE: 3

Gln His Trp Ser Tyr Gly Leu Arg Pro Gly
1               5                   10

<210> SEQ ID NO 4
<211> LENGTH: 10
<212> TYPE: PRT
<213> ORGANISM: Homo sapiens
<220> FEATURE:
<223> OTHER INFORMATION: mLHRH

<400> SEQUENCE: 4

Gln His Trp Ser Trp Gly Leu Arg Pro Gly
1               5                   10

<210> SEQ ID NO 5
<211> LENGTH: 33

```
<212> TYPE: PRT
<213> ORGANISM: Homo sapiens
<220> FEATURE:
<223> OTHER INFORMATION: JCHmLHRH

<400> SEQUENCE: 5

Gln His Trp Ser Trp Gly Leu Arg Pro Gly Phe Ala Leu Ala Leu Lys
1               5                   10                  15

Ala Leu Lys Lys Ala Leu Lys Lys Leu Lys Lys Ala Leu Lys Lys Ala
            20                  25                  30

Leu

<210> SEQ ID NO 6
<211> LENGTH: 33
<212> TYPE: PRT
<213> ORGANISM: Homo sapiens
<220> FEATURE:
<223> OTHER INFORMATION: JC21mLHRH

<400> SEQUENCE: 6

Gln His Trp Ser Trp Gly Leu Arg Pro Gly Ala Phe Lys Lys Ala Phe
1               5                   10                  15

Lys Lys Ala Lys Lys Ala Phe Lys Lys Ala Phe Lys Ala Phe Ala Phe
            20                  25                  30

Ala

<210> SEQ ID NO 7
<211> LENGTH: 33
<212> TYPE: PRT
<213> ORGANISM: Homo sapiens
<220> FEATURE:
<223> OTHER INFORMATION: JCHLHRH

<400> SEQUENCE: 7

Gln His Trp Ser Tyr Gly Leu Arg Pro Gly Phe Ala Leu Ala Leu Lys
1               5                   10                  15

Ala Leu Lys Lys Ala Leu Lys Lys Leu Lys Lys Ala Leu Lys Lys Ala
            20                  25                  30

Leu

<210> SEQ ID NO 8
<211> LENGTH: 33
<212> TYPE: PRT
<213> ORGANISM: Homo sapiens
<220> FEATURE:
<223> OTHER INFORMATION: JC21LHRH

<400> SEQUENCE: 8

Gln His Trp Ser Tyr Gly Leu Arg Pro Gly Ala Phe Lys Lys Ala Phe
1               5                   10                  15

Lys Lys Ala Lys Lys Ala Phe Lys Lys Ala Phe Lys Ala Phe Ala Phe
            20                  25                  30

Ala
```

LYTIC PEPTIDES HAVING ANTI-PROLIFERATIVE ACTIVITY AGAINST PROSTATE CANCER CELLS

STATEMENT REGARDING FEDERALLY SPONSORED RESEARCH OR DEVELOPMENT

This invention was made with government support under PC073977 awarded by the Department of Defense and under 1 U54 CA118623-01 awarded by the NIH National Cancer Institute. The government has certain rights in the invention.

FIELD OF THE INVENTION

The present invention relates to lytic peptides having anti-proliferative activity against prostate cancer cells, genes for encoding the same, and methods and uses thereof in the treatment of prostate cancer. More particularly, the present invention relates to fusion proteins that target prostate cancer cells, which proteins comprise a lytic peptide bound to luteinizing hormone-releasing hormone or modified version of luteinizing hormone-releasing hormone, genes for encoding the same, and methods and uses thereof in the treatment of prostate cancer.

BACKGROUND OF THE INVENTION

In the United States, prostate cancer is currently the most commonly diagnosed cancer and the second-leading cause of cancer death in men. Following earlier trends of fluctuating rates, prostate cancer rates have been since 2001 decreasing by 4.4% per year. Likewise, since the early 1990s, there has been a more substantial decrease in prostate cancer deaths among African American men than their white counterparts. Yet prostate cancer incidence and death rates among African Americans remain more than twice as high as those for whites. Furthermore, African American men and Jamaican men of African descent have the highest incidences of prostate cancer in the world. Many factors have been suggested to contribute to the higher prostate cancer incidence and mortality rates in African American men. For these men, overexpression of the androgen receptor ("AR") and elevated luteinizing hormone ("LH") levels have been associated with advanced disease progression. Although substantial efforts have been applied to identify agents with efficacy against prostate cancer, few treatment options, including classical chemotherapeutic agents, have not proven to be effective against this disease.

Lytic peptides are a ubiquitous feature of nearly all multicellular and some single-cellular life forms. They generally consist of between 10 and 40 amino acid sequences, which have potential for forming discrete secondary structures. Often, they exhibit the property of amphipathy (having both hydrophilic and lipophilic properties) because they may be depicted as a cylinder with one curved face composed primarily of nonpolar amino acids, while the other face is composed of polar amino acids. Most lytic peptides that have been previously described, appear to fall into one of three different classes based on the arrangement of amphipathy and high positive charge density within the molecule: Cecropins (35 amino acids in length and derived from the Giant Silk Moth), Magainins (23 amino acids in length and derived from the African Clawed Frog), and Melittin (26 amino acids in length and derived from the Honeybee). The conservation of these physical properties is a requisite for activity, but the requirements seem to be somewhat nonspecific in terms of amino acid sequence.

Recently, the design and use of lytic peptides for numerous cancers has been reported, including for prostate cancer. (See, for example, Hansel et al., "Conjugates of lytic peptides and LHRH or betaCG target and cause necrosis of prostate cancers and metastases," Mol Cell Endocrinol 2007; 269:26-33, and Leuschner et al., "Human prostate cancer cells and xenografts are targeted and destroyed through luteinizing hormone releasing hormone receptors," Prostate 2003; 56:239-49. Also, U.S. Pat. No. 6,635,740, issued to Enright et al., discloses amphipathic lytic peptides that comprise a ligand domain and a cytotoxin domain which may be used to target tumors, such as prostate cancer tumors, by using a hormone upon which the tumor is dependent as the ligand domain. The research of Hansel and Leuschner utilizing lytic peptides conjugated with luteinizing hormone-releasing hormone ("LHRH") has indicated the importance of a steroid presence (see also, Leuschner et al., "Targeting breast and prostate cancers through their hormone receptors." Biol. Reprod. 2005; 73:860-5; Hansel et al., "Targeted destruction of prostate cancer cells and xenografts by lytic peptide-betaLH conjugates." Reprod. Biol. 2001; 1:20-32; Hansel et al., "Destruction of breast cancers and their metastases by lytic peptide conjugates in vitro and in vivo." Mol. Cell. Endocrinol. 2007; 260-262:183-9; and Leuschner et al., "Membrane disrupting lytic peptide conjugates destroy hormone dependent and independent breast cancer cells in vitro and in vivo." Breast Cancer Res. Treat. 2003; 78: 17-27). Namely, the work of those researchers indicate that presence of a circulating estradiol or follicle-stimulating hormone is necessary for their lytic compounds to be active; the removal of the steroids that they used from the culture media eliminated the sensitivity of prostate cancer cells to the effects of their lytic peptide-LHRH conjugates. It would be desirable if lytic peptides were identified that were highly active and non-toxic absent a hormone presence.

Early stage prostate cancers are androgen dependent, and thus can be treated in part via hormone therapy. Most hormone dependent cancers become refractory (i.e., hormone independent) after one to three years and resume growth despite hormone therapy. Hormone-refractory prostate cancer is a late stage of prostate cancer for which better treatments are needed. Thus, therapies directed at preventing or limiting the tumor's transition to the more aggressive invasive and metastatic stages offer benefits different from the present therapies that were designed to kill prostate cancer cells.

Thus, there remains a need in the art for improved treatments for prostate cancer that are highly effective in causing disease remission and in preventing progression of the disease to more advanced and aggressive stages while still exhibiting low toxicity.

SUMMARY OF THE INVENTION

In light of the above needs, it is an object of the present invention to identify lytic peptides with anti-proliferative activity against cancer cells.

Furthermore, it is an object of the present invention to provide new treatments for treating patients with prostate cancer, including hormone refractory prostate cancer.

Additionally, it is an object of one or more embodiments of the present invention to provide lytic peptides that in the absence of a hormone presence are nonetheless highly active against prostate cancer and non-toxic.

The various embodiments of the present invention achieve these and other objects via the discovery of novel compounds that exhibit lytic activity against cancer cells and, in particular, exhibit activity in inhibiting prostate cancer cell proliferation. The lytic peptides according to the invention have centers of hydrophobicity that have been altered from previously designed peptides and their positive charge density increased in order to maximize physical properties known to enhance cancer cell killing activity. After synthesis, the efficacy of the peptides according to the invention in inhibiting cancers, and prostate cancer in particular, was confirmed using a prostate cancer progression model that measured the effect of the peptides on androgen-responsive LNCaP cancer cells, androgen-unresponsive DU-145 cancer cells, and androgen-unresponsive PC-3 cancer cells to approximate the stages of prostate cancer progression. The effect of the peptides on non-cancerous cells was also analyzed to determine potential toxicity.

Two preferred synthetic lytic peptides according to the invention named JCH and JC21 comprise 23-amino acid sequences which are, respectively, SEQ. ID NO. 1 and SEQ. ID NO. 2. Both JCH and JC21 inhibit cancer cell proliferation at low concentrations according to the model described above. Further, since prostate cancer cells express high levels of luteinizing hormone-releasing hormone receptors ("LHRH-Rs") and since LHRH-Rs may be used as a target for hormonal therapy, applicants identified that lytic peptides according to the invention, including JCH and JC21, can be chemically bound to other peptides that bind with LHRH-R. These other peptides may include LHRH having the sequence SEQ. ID NO. 3, or, preferably, a modified LHRH named mLHRH discovered by Applicants and having the sequence SEQ. ID NO. 4. Thus, JCH and JC21 were linked with a modified LHRH binding sequence for enhanced tumor targeting through LHRH-R. The resulting larger peptides were designated JCHmLHRH and JC21mLHRH, and have amino acid sequences that are, respectively, SEQ. ID NO. 5 and SEQ. ID NO. 6. While experimental data indicates that human prostate cancer cell lines were sensitive to both lytic peptides that were so-conjugated to target LHRH-R and non-conjugated lytic peptides, Applicants have surprisingly found that both JCHmLHRH and JC21mLHRH have enhanced anti-proliferative activity against cancer cells in comparison to un-conjugated JCH and JC21. Thus, preferred embodiments of the invention comprise compounds JCHmLHRH, JC21mLHRH, and other lytic peptides so-conjugated with mLHRH and their respective use in the treatment of cancers such as prostate cancer.

In this regard, one embodiment of the invention includes compounds that comprise a first domain and a second domain, wherein: (a) the first domain comprises a ligand peptide that binds to LHRH-R; and (b) the second domain comprises a lytic peptide, where the lytic peptide has a sequence selected from the group consisting of SEQ. ID NO. 1 and SEQ. ID NO. 2. For such compounds, the ligand peptide may be, for example, LHRH having the sequence SEQ. ID NO. 3, or, preferably mLHRH having the sequence SEQ. ID NO. 4.

Another embodiment of the invention includes compounds that comprise a first domain and a second domain, wherein: (a) the first domain comprises mLHRH having the sequence SEQ. ID NO. 4, and (b) the second domain comprises a lytic peptide, where said lytic peptide is from 10 to 40 amino acids in length and has anti-proliferative activity against tumor cells that express elevated levels of LHRH-R. Preferably, the lytic peptides in this embodiment cause shrinkage of the cell walls of cancer tumor cells, and, most preferably, comprise one of JCH (SEQ. ID NO. 1) or JC21 (SEQ. ID NO. 2).

The compounds according to any of the embodiments above may include only the first and second domains, or may further and optionally comprises one or more additional domains or portions, wherein such an additional domain or portion may serve as a carrier to facilitate uptake by the intestine when the compound is administered orally to said mammal (such as vitamin B12), serve to link different domains/portions together, or target specific cells, receptors, or other biologic targets. Further, peptide domains may be joined in either order such that either the first domain or the second domain may be closer to, or comprise, either terminus. Preferably, the compound peptides according to this embodiment of the invention have the first domain bonded directly to said second domain without an intermediate linking domain joining the first and second domains.

Additionally, embodiments of the invention may comprise compounds having a first domain with the sequence SEQ. ID NO. 1 or SEQ. ID NO. 2. Optionally, such compounds may further comprises one or more additional domains or portions as described above, including carrier domains/portions to facilitate uptake by the intestine when the compound is administered orally to said mammal (such as vitamin B12), linking domains/portions, or domains/portions to target specific cells, receptors, or other biologic targets.

As each of the various compounds described above as comprising alternative and preferred embodiments of the invention have anti-proliferative activity, further aspects of the invention further include methods for inhibiting tumor cell proliferation in a mammal, comprising administering to the mammal an effective amount one or more of the of the compounds of the invention. Such methods for inhibiting according to the invention preferably are for inhibiting proliferation of tumor cells in a mammal where said tumor cells express elevated levels of LHRH-R, are for mammals diagnosed as having a prostate cancer tumor, and/or are for treating human patients. Further, any of said methods may include administration of the compound to the mammal in any suitable fashion, including, for example, orally, intravenously, or parenterally.

As such, additional embodiments of the invention comprise pharmaceutical products that comprise a pharmaceutically effective amount of at least one compound according to the invention and a carrier. Additionally, the compounds of the present invention may be administered as described, or as pharmaceutically acceptable salts thereof.

The pharmaceutical products may be of any conventional form known in the art, including oral formulations, injectable formulations, transdermal formulations, transmucosal formulations, intravenous formulations, and the like.

For each of the various compounds described above as comprising alternative and preferred embodiments of the invention, other aspects of the invention further include polynucleotides that have an encoding region that encodes that compound, recombinant vectors which include those polynucleotides, and transformants that have inserted therein one or more of those recombinant vectors. Further, additional aspects of the invention include methods for producing one or more of the various compounds according to invention, which methods each include the step of culturing a transformant as described above so as to induce the transformant to produce at least one compound of the invention.

The various embodiments of the invention having thus been generally described, several illustrative embodiments will hereafter be discussed with particular reference to several attached drawings and in view of various experimental examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1B:
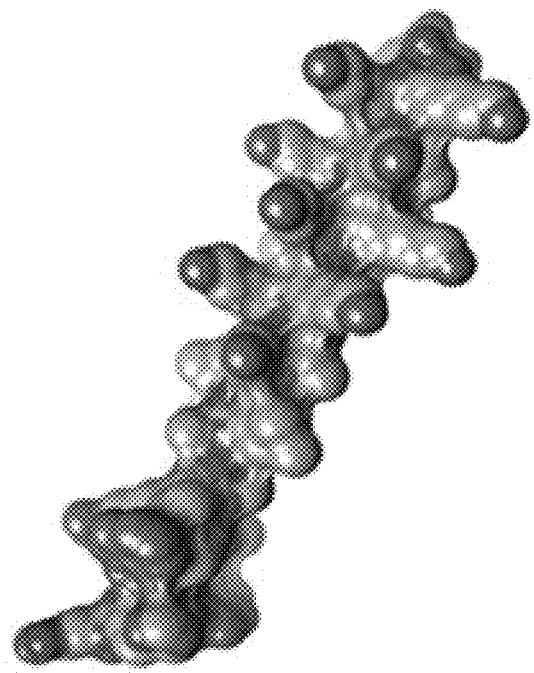
FIG. 1A through FIG. 1D are color drawings showing three-dimensional molecular modelings of peptides JC21mLHRH, JCHmLHRH, LHRH, and mLHRH, respectively.
Figure 1A:
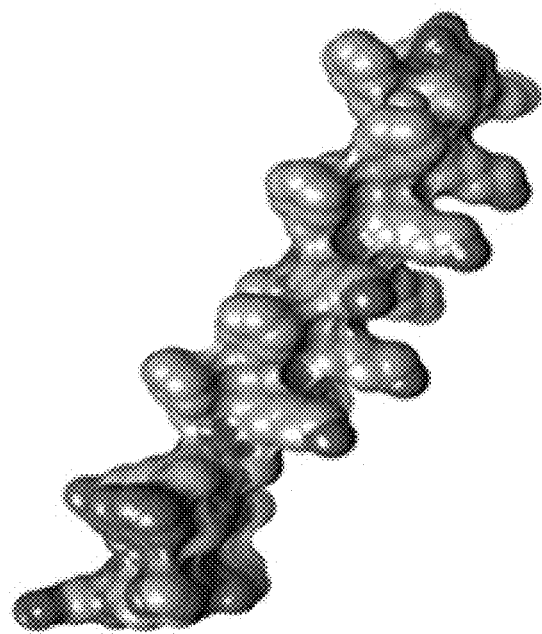
Figure 1D:
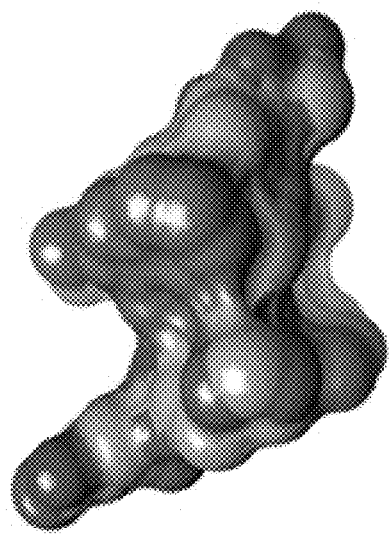
Figure 1C:
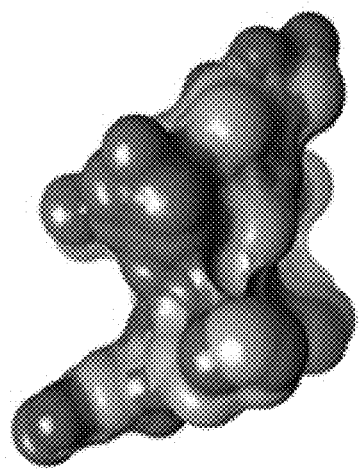

As used herein "effective amount" of a composition is an amount sufficient to kill the targeted cells in a background population of non-targeted cells. Where appropriate in context, a "pharmaceutically effective amount" of a composition is an amount that is sufficient to kill the targeted cells, inhibit proliferation of the targeted cells, or initiate remission of a targeted cancer when that amount is administered to a stricken animal as a pharmaceutical formulation.

Polynucleotides of the invention include any polynucleotide having a nucleotide sequence that encodes the peptides of the invention, although DNA is preferred. Exemplary DNA includes genomic DNA, genomic DNA libraries, cellular or tissue cDNA, cellular or tissue cDNA libraries, and synthetic DNA. The vectors used in the libraries are not subject to any particular limitation, and may be, for example, bacteriophages, plasmids, cosmids or phagemids. Also, amplification may be carried out directly by a reverse transcription polymerase chain reaction (abbreviated below as "RT-PCR") using total RNA or a mRNA fraction prepared from the above-mentioned cell or tissue.

Other hybridizable polynucleotides include, when calculations are done with a sequencing program such as FASTA or BLAST using the default parameters, DNA that is at least approximately 60%, at least approximately 65%, at least approximately 70%, at least approximately 75%, at least approximately 80%, at least approximately 85%, at least approximately 88%, at least approximately 90%, at least approximately 92%, at least approximately 95%, at least approximately 97%, at least approximately 98%, at least approximately 99%, at least approximately 99.3%, at least approximately 99.5%, at least approximately 99.7%, at least approximately 99.8%, or at least approximately 99.9% identical to polynucleotides encoding the subject amino acid sequence. The identity of an amino acid sequence or a nucleotide sequence can be determined using the above-described method.

Recombinant vectors of the invention include those that may be obtained by ligating (inserting) the polynucleotides of the invention to a suitable vector. More specifically, the recombinant vector may be obtained by cleaving purified polynucleotide (e.g., DNA) with a suitable restriction enzyme, then inserting the cleaved polynucleotide to a restriction enzyme site or multicloning site on a suitable vector, and ligating the polynucleotide to the vector. The vector for inserting the inventive polynucleotide is not subject to any particular limitation, provided it is capable of replication in the host. Vectors that may be used for this purpose include plasmids, bacteriophages, and animal viruses. Illustrative examples of suitable plasmids include plasmids from *E. coli* (e.g., pBR322, pBR325, pUC118 and pUC119), plasmids from *Bacillus subtilis* (e.g., pUB110 and pTP5), and plasmids from yeasts (e.g., YEp13, YEp24 and YCp50). An example of a suitable bacteriophage is the λ phage. Examples of suitable animal viruses include retroviruses, vaccinia viruses and insect viruses (e.g., baculoviruses).

Transformants of the invention include can those that may be created by introducing into a suitable host the recombinant vector, obtained as described above, which includes a polynucleotide of the invention (i.e., a polynucleotide encoding a peptide of the invention). The host is not subject to any particular limitation, provided it is capable of expressing the polynucleotide of the invention. Examples include bacteria of the genera *Escherichia, Bacillus, Pseudomonas* and *Rhizobium*, yeasts, animal cells and insect cells.

Introduction of the recombinant vector into the host and transformation thereby may be carried out by any of various commonly used methods. Examples of suitable methods for introducing the recombinant vector into the host cell include the calcium phosphate method (Virology, 52, 456-457 (1973)), lipofection (Proc. Natl. Acad. Sci. USA, 84, 7413 (1987)), and electroporation (EMBO J., 1, 841-845 (1982)). Examples of methods for transforming genus *Escherichia* bacteria include the methods described in Proc. Natl. Acad. Sci. USA, 69, 2110 (1972), and Gene, 17, 107 (1982). Methods for transforming genus *Bacillus* bacteria include the methods described in Molecular & General Genetics, 168, 111 (1979). Methods for transforming yeasts include the methods described in Proc. Natl. Acad. Sci. USA, 75, 1929 (1978). Methods for transforming animal cells include the methods described in Virology, 52, 456 (1973). Methods for transforming insect cells include the methods described in Bio/Technology, 6, 47-55 (1988). A transformant created by transformation with a recombinant vector containing the polynucleotide which codes for the peptide of the invention (i.e., the polynucleotide of the invention) may be obtained in this way.

One skilled in the art will understand that the subject peptides may be produced by culturing transformants of the invention under conditions that allow the polynucleotide encoding the peptide to be expressed, thereby inducing formation and accumulation of the inventive peptide, then isolating and purifying the peptide. It is well within the skill of one of ordinary skill in the art to select the appropriate conditions for causing expression for a given transformant, and to implement suitable mechanisms for isolating and purifying the peptide. The transformant of the invention may be cultivated by a conventional method used for culturing hosts. In such cultivation, the peptide of the invention may be formed by the transformant and accumulates within the transformant or the culture broth, requiring the selection of suitable isolation and purification processes.

The novel lytic peptides of the invention were designed by Applicant to have centers of hydrophobicity that have been altered from previously designed peptides and their positive charge density increased in order to maximize physical properties known to enhance cancer cell killing activity. After synthesis, the efficacy of the peptides according to the invention in inhibiting cancers, and prostate cancer in particular, was confirmed via experimental analysis of the efficacy of the peptides in a prostate cancer progression model to inhibit prostate cancer. The effect of the peptides on non-cancerous cells was also analyzed to determine potential toxicity.

Two new peptides, JCH (SEQ. ID NO. 1) and JC21 (SEQ. ID NO. 2) were identified as having centers of hydrophobicity that were altered from previous peptides to alter their respective physical properties (charge, density, length, amphipathy, and spatial orientation) and thereby increase lytic activity on cancer cells To achieve this, two peptide sequences, designated JCH and JC21, were synthesized. Since prostate cancer cells express high levels of luteinizing hormone-releasing hormone receptors ("LHRH-Rs"), which may serve as a target for hormonal therapy, JCH and JC21 were linked with a modified LHRH binding sequence ("mLHRH") for enhanced tumor targeting. The resulting conjugated products, designated JCHmLHRH (SEQ. ID NO. 4) and JC21mLHRH (SEQ. ID NO. 5), were also obtained to target LHRH-R. FIG. 1A through FIG. 1D are three-dimensional molecular modelings of peptides JC21mLHRH, JCHmLHRH, LHRH, and mLHRH, respectively, derived using the UCSF molecular modeling program Chiron. The colored atoms in FIG. 1A through 1D are the following: carbon is shown in gray, nitrogen in blue, and oxygen in red. The amino acid residue tyrosine (in the natural LHRH sequence depicted by FIG. 1C) is purple, while as shown the sequence of mLHRH possesses an additional tryptophan in place of this tyrosine (all tryptophans in FIG. 1A through FIG. 1D are colored green).

To evaluate the efficacy of these peptides in inhibiting prostate cancer, a prostate cancer progression model was followed that utilized several different cell lines in various experiments as described herein to form this model, including the known cell lines DU-145, PC-3, LNCaP, and hPrEC. DU-145 is a cell line originally derived from a brain metastasis of a human prostate adenocarcinoma that retains the androgen independence of the original tumor and does not express a functional AR. This cell line has both LHRH-R and epidermal growth factor receptors ("EGFR"), and produces the EGFR ligands, transforming growth factor α (TGF-α) and EGF. The androgen-unresponsive PC-3 cell line is derived from a human bone metastasis of a grade IV prostatic adenocarcinoma, while the androgen-responsive LNCaP cell line is derived from a human lymph node metastasis. For all experiments described herein, normal primary human prostate epithelial cells ("hPrEC") were obtained from Clonetics (Lonza Inc., Walkersville, Md.), while the other cell lines were purchased from ATCC and maintained in T-media (Gibco Invitrogen, CA) supplemented with 10% fetal bovine serum (FBS) (Gibco Invitrogen, CA) and 1% penicillin/streptomycin (Cellgro Mediatech, Inc., VA).

Through the utilization of androgen-responsive LNCaP cells, and androgen unresponsive DU-145 and PC-3 prostate cancer cells, this model approximates different stages of prostate cancer progression. Applicant's experiments yielded evidence that peptides JCH and JC21 inhibit cell proliferation at low concentrations, and, when conjugated with a modified LHRH sequence, the resulting peptides have enhanced antiproliferative activity. Furthermore, conjugated peptides JCHmLHRH and JC21mLHRH were found to have minimal antiproliferative effects on normal prostate cells.

In the various experiments described below, unless otherwise noted, the subject synthetic peptides according to the present invention were synthesized by Chem Prep Inc. (Miami, Fla.) and were determined to be 95% pure by HPLC. For experimental use, the peptides were dissolved in sterile water. Samples of JCHmLHRH and JC21mLHRH were confirmed as containing 33 amino acids, and their molecular weights were measured as 3742.73 and 3150.36, respectively.

In the various experiments described below, unless otherwise noted, the cytotoxicity of the various peptides when measured was evaluated using the methylthiazol tetrazolium ("MTT") assay (Sigma Aldrich, MO), which determines the number of viable cells from the formazan crystals produced by metabolic activity. The cells in such cytotoxicity experiments were plated in 96-well plates at $2.5 \times 10^3$ cells/well, and were allowed to reattach overnight. They were then exposed to the test lytic peptides (1-20 µM) for 72 h. The MTT reagent [3-(4,5-dimethylthiazol-2-yl)-2,5-diphenyltetrazolium bromide], 50 µL) in T-media was added to each well, and the plates were incubated for 2 h. The supernatant media was aspirated, and formazan crystals were dissolved with 100 mL dimethylsulfoxide per well at 37° C. for 10 min. The quantity of solublized formazan per well was determined by a Spectromax plate reader at 540 nm (Molecular Devices, CA). Each assay was performed at least three times with six replicates per data point.

In the various experiments described below, unless otherwise noted, real-time imaging of cell cultures was performed utilizing an Olympus DSU (Disk Scanning Units) Confocal microscope (Olympus America Inc., PA). The subject cells were maintained in 5% $CO_2$ at 37° C. in an incubation chamber (Pathology Devices, Inc., MD). Images were taken every 15 min and processed utilizing MetaMorph Imaging Software (Molecular Devices, CA).

In the various experiments described below, unless otherwise noted, co-cultures were prepared and utilized as described by Yates et al. (see Yates C, Shepard C R, Papworth G, Dash A, Beer Stolz D, Tannenbaum S, et al., Novel three-dimensional organotypic liver bioreactor to directly visualize early events in metastatic progression, Adv Cancer Res, 2007; 97:225-46; and Yates C, Shepard C R, Stolz D B, Wells A., Co-culturing human prostate carcinoma cells with hepatocytes leads to increased expression of E-cadherin, Br J Cancer 2007; 96:1246-52), with certain modifications as noted herein. The co-cultures consisted of 50,000 cells/cm² of GFP-HS-27a bone marrow stromal cells and 2000 cells/cm² of red fluorescent protein PC-3 prostate cancer cells ("RFP-PC-3"), and were maintained in Dulbecco's modified Eagle medium, and cell death was monitored in real-time (as described above) by differential fluorescence. To determine relative intensity, the total intensity area of each image as well as the threshold intensity for each channel was measured utilizing Metamorph Imaging Software (Molecular Devices, Inc., CA), and the significance between the two intensities was then analyzed statistically. All quantitative data was normalized to each control image.

For all experiments, unless otherwise noted, statistics were performed with Microsoft Excel. Independent Student's t-test was utilized to determine statistical differences between experimental subjects and control subjects. The $IC_{50}$ values were derived through regression analysis of the continuous data by cubic spline interpolation utilizing Aabel™ (Gigawiz Ltd. Co., OK), a software application that integrates statistics (inferential and multivariate) with graphical representation.

Several preferred embodiments of the various inventions of the present invention will now be described and illustrated with respect to several laboratory experiments and associated laboratory data.

Example 1

To determine the effectiveness of JCH and JC21 with or without mLHRH conjugates, androgen-independent, highly metastatic PC-3 cells were exposed to the peptides in increasing concentrations (0-20 μM). The results of this experiment are reported in the table provided at FIG. 2A. Generally, both peptides exhibited a dose-dependent decrease in cell proliferation against the PC-3 cells, with JCH and JC21 having $IC_{50}$ values of 6.67 and 9.25 μM, as reported in FIG. 2A.

A procedure was repeated for peptides JCHmLHRH and JC21mLHRH against PC-3 cells, and also extended for those two peptides against LNCaP cells and DU-145 cells. The table of FIG. 2A also shows the determined $IC_{50}$ values for these two mLHRH-conjugated peptides of the present invention as obtained against cultures of these various prostate cancer cell lines. As shown in the table, conjugation of JCH and JC21 to mLHRH made the lytic peptides more active against the PC-3 cells, lowering the $IC_{50}$ concentrations to 4.22 μM for JCHmLHRH and 7.24 μM for JC21mLHRH. Further, JCHmLHRH and JC21mLHRH were active against two additional human prostate cell lines, the androgen-dependent LNCaP and androgen-independent DU-145 cell lines. As reported in the table, the $IC_{50}$ values for LNCaP cells were 4.36 μM for JCHmLHRH and 9.15 μM for JC21mLHRH, while for the DU-145 cells, the values were 4.81 μM for JCHmLHRH and 5.66 μM for JC21mLHRH. All $IC_{50}$ values are summarized in FIG. 2A.

For this experiment, $IC_{50}$ values were determined by interpolation of three individual experiments performed in quadruplicate at 50% cell death. All values were reported in the table of FIG. 2A were determined to be significant compared to control p<0.001. In the table, "n.d." serves as an abbreviation for "not determined," as tests were not conducted for JHC and JC21 against LNCaP and DU-145.

Figures 2A, 2B:
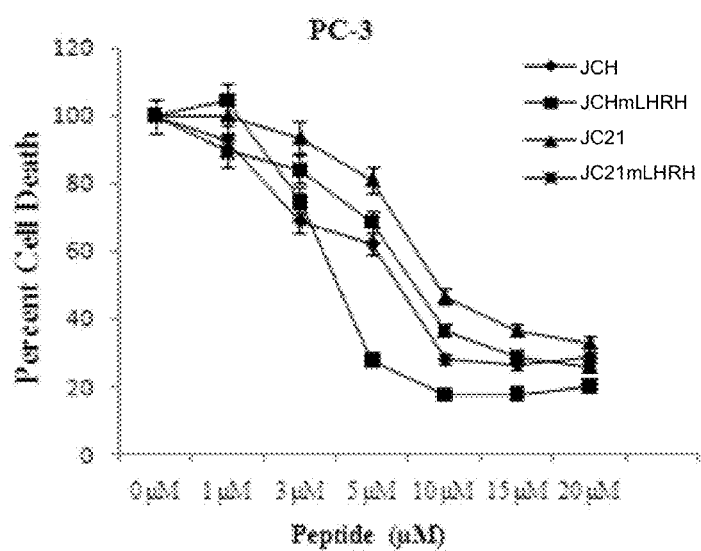
FIG. 2A is a table reporting experimental results for $IC_{50}$ values for various peptides of the present invention as obtained against cultures of various prostate cancer cell lines.
FIG. 2B through FIG. 2D are graphs comparing experimental results for the cytotoxicity of JC21, JCH, JC21mLHRH, and JCHmLHRH for prostate cancer cell lines PC-3, LNCaP, and DU-145, respectively.
Figure 2C:
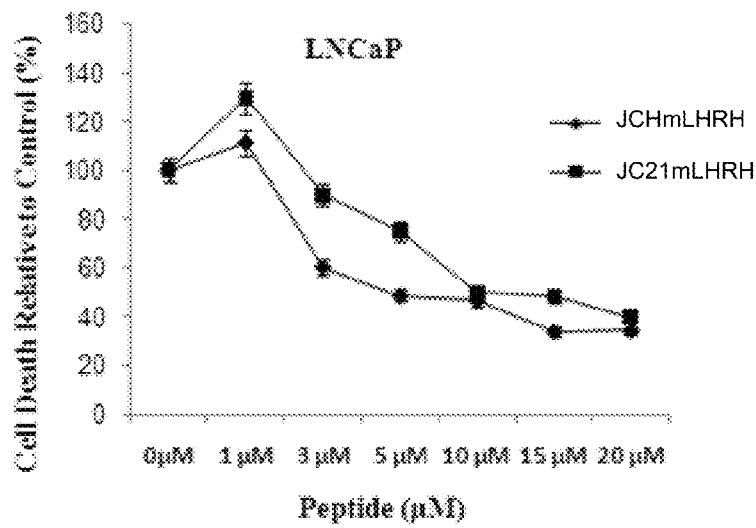
Figure 2D:
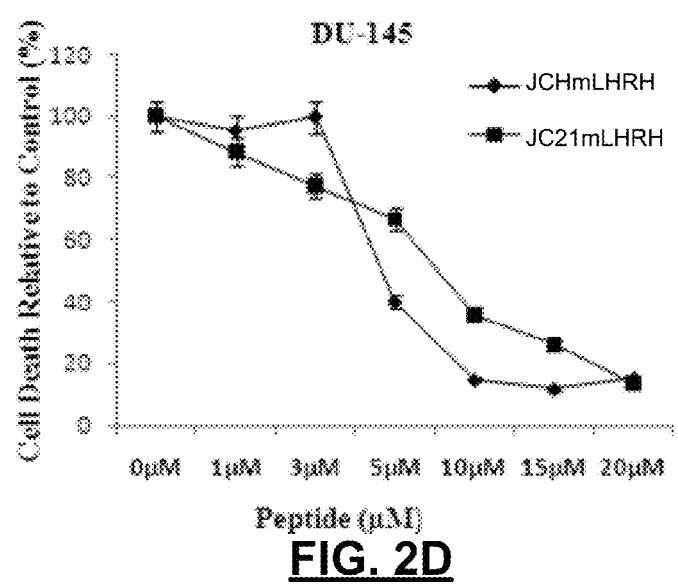

FIG. 2B through FIG. 2D are graphs reporting the cytotoxicity of JC21, JCH, JC21mLHRH, and JCHmLHRH for prostate cancer cell lines PC-3, LNCaP, and DU-145, respectively, as determined in this Experiment at various concentrations of the peptides. As reported in these graphs, cell viability was determined by MIT, mean±s.d. (n=4). It can be seen from these three graphs that JCH, JC21, JCHmLHRH, and JC21mLHRH all inhibit cell proliferation at relatively low concentrations, and exhibit a typical dose-dependent relationship.

The results of the experiment described in Example 1 provided similar $IC_{50}$ values and dose-dependent relationships for the peptides across the three different prostate cancer cells lines. Thus, it was determined that other tests would likewise have similar results across the different cell lines, making it possible to perform further tests and experiments with only a single prostate cancer cell line and reasonably assume that similar results would be obtained against the other lines.

Example 2

Figure 3A:
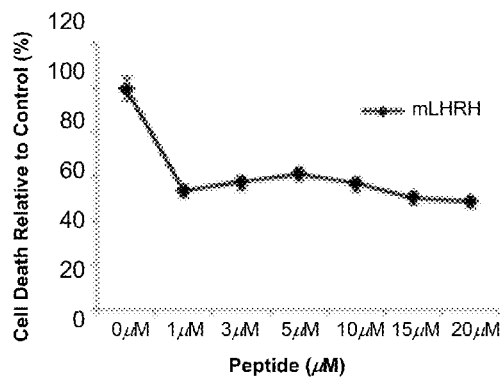
FIG. 3A and FIG. 3C are graphs reporting experimental results for the cytotoxicity of mLHRH on PC-3 cells.

To determine if the addition of the mLHRH sequence was directly responsible for the increased activity of both JCHmLHRH and JC21mLHRH against PC-3 as reported in FIG. 2A, the anti-proliferative (anti-growth) effectiveness of the mLHRH sequence alone was tested. Using a similar procedure as above in Example 1, it was found that the mLHRH sequence caused a decrease in cell proliferation of PC-3 cells at concentrations as low as 1 μM, but that higher concentrations failed to cause 50% cell death. The chart of FIG. 3A shows the measured cytotoxicity of the mLHRH sequence alone at various concentrations of the peptide as determined by this experiment. The data shown in this chart represents an average of three individual experiments performed in quadruplicate, where cell viability was determined by MIT, mean±s.d. (n=3). Although mLHRH activity was not as potent as JC21mLHRH and JCHmLHRH, the sensitivity to PC-3 cells was sustained, providing evidence that addition of the LHRH sequence adds to lytic activity.

Thus, the mLHRH sequence can foreseeably be used in conjugation with other lytic peptides having activity against prostate cancers or other cancers which express elevated levels of LHRH-R.

Example 3

To more firmly establish the significance of the mLHRH sequence on peptide activity, PC-3 cells were treated with siRNA-LHRH at 50 nM and 100 nM concentrations and assayed LHRH levels by immunofluorescence. In this Experiment, PC-3 cells were treated with siRNA-LHRH-R at 50 nM and 100 nM, and compared to control. For this experiment, a total of about $2 \times 10^5$ cells, equaling approximately 60-70% confluency, were plated in six-well plates. The LHRH-R siRNA (Santa Cruz, Calif.) was diluted in 200 ml of Opti-MEM (Invitrogen, CA). A 4 ml aliquot of Lipofectamine 2000 (Invitrogen, CA) was diluted in 200 ml of Opti-MEM and incubated for 5 min at room temperature. The diluted siRNA and Lipofectamine 2000 were mixed according to manufacturer's directions and incubated for 20 min at room temperature. The resulting complexes were added to each well and incubated for 24 h. Media were changed after 24 h, and replaced with fresh media and incubated for an additional 24 h.

LHRH-R expression was determined by immuno-fluorescence staining with 4',6-diamidino-2-phenylindole ("DAPI") utilizing anti-LHRH-R antibody (Lab Vision, CA) and Alexa 488 secondary antibody (Invitrogen, CA). As shown in the immuno-fluorescence photographs of FIG. 3B, 100 nM siRNA-LHRH exhibited the most significant decreases in LHRH levels as determined by lack of fluorescent staining.

Figure 3C:
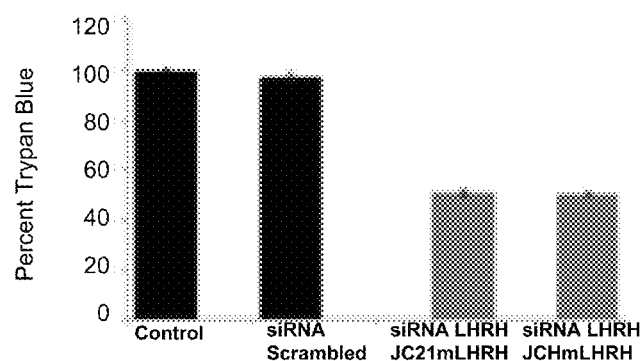
Figure 3B:
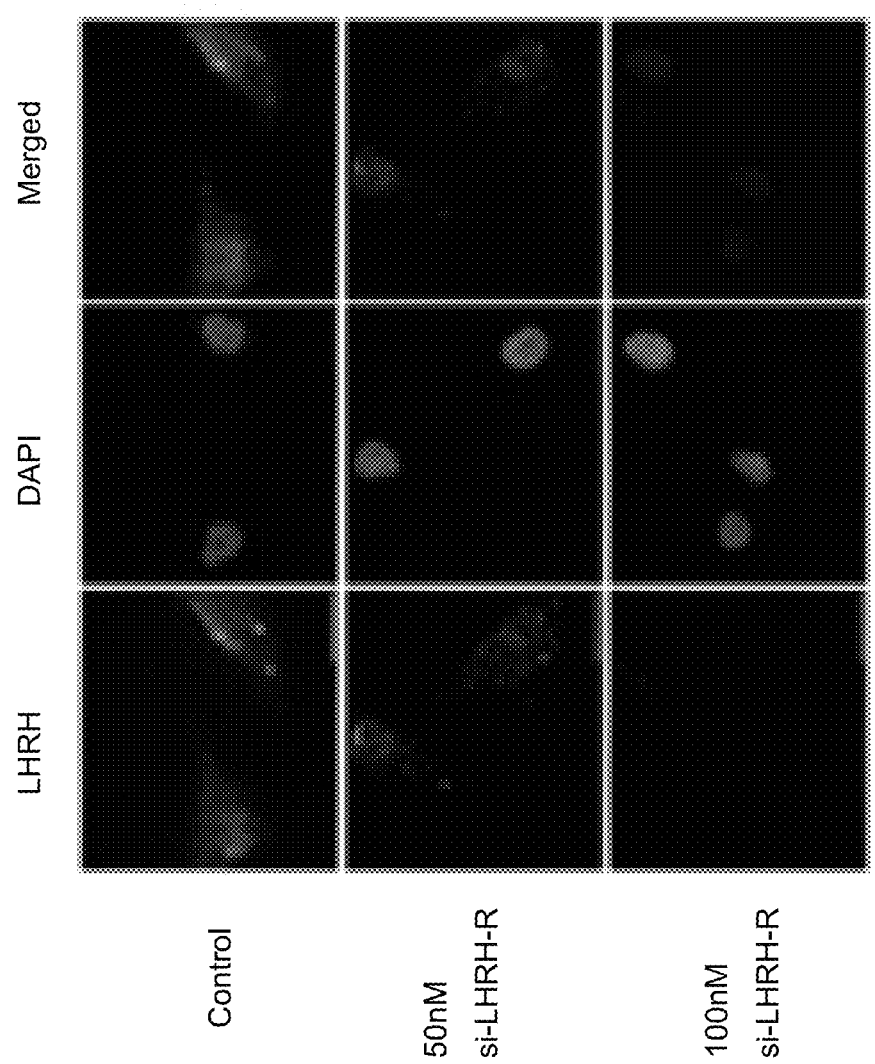
FIG. 3B is a table displaying nine color photographs that show differential immuno-fluorescence results for representative samples of PC-3 cells treated with siRNA-LHRH-R relative to control.

For purposes of comparison, PC-3 cells were treated with JC21 mLHRH or JCHmLHRH in the presence or absence of 100 nM siRNA-LHRH-R or siRNA-scramble treated cells. Cell viability was determined by trypan blue exclusion, and the results are depicted in the graph of FIG. 3C. The values in this graph are representative of three independent experiments (n=3), and the data shows that depletion of LHRH levels decreased the sensitivity of both peptides sequences by 50%

Example 4

Figure 4:
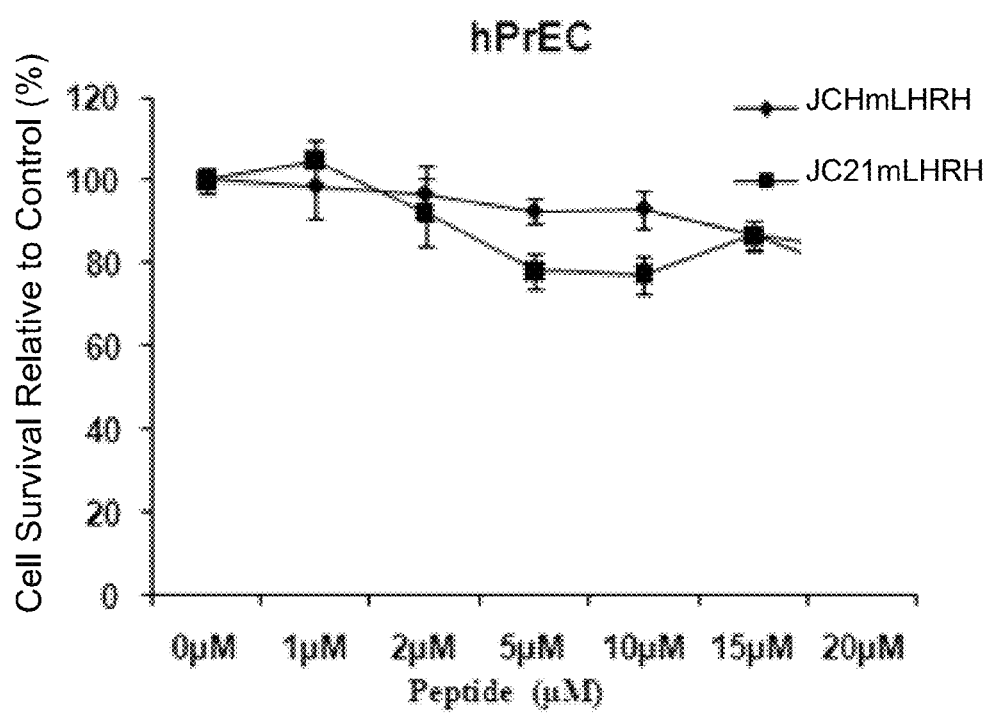
FIG. 4 is a graph comparing experimental results for the cytotoxicity of JCHmLHRH or JC21mLHRH on normal primary hPrEC cells.

To determine the selectivity of JC21mLHRH and JCHmLHRH, non-cancerous hPrEC cell cultures were exposed to various concentrations of JCHmLHRH and JC21mLHRH to measure dose dependent cell toxicity of the peptides. The hPrEC cells were exposed to JCHmLHRH or JC21mLHRH at 0-20 µM. For each concentration of peptide, cell survival relative to control was measured after administration (cell viability was determined by MTT; Mean±s.d. (n=4)). FIG. 4 is a graph depicting experimental data for this experiment, showing the cytotoxicity of JCHmLHRH and JC21mLHRH to normal primary hPrEC cells increases as the concentration of the peptides increase, but the correlation is not very strong, and neither JCHmLHRH nor JC21mLHRH causes appreciable decreases in hPrEC cell proliferation. This finding supports a conclusion that JCHmLHRH and JC21mLHRH will not exhibit unacceptable levels of toxicity to non-cancerous cells.

Example 5

Although the mechanism associated with the anti-tumor activity of lytic peptides has not been defined, without wishing to be limited to any mechanism of action, it is believed that direct interaction of the present lytic peptides with the cell membrane causes the electrochemical potential to collapse, resulting in cell death. To investigate the potential mechanism of action, a qualitative approach utilizing real-time imaging was employed in conjunction with monitoring of a classic marker of apoptosis, Annexin V. Since the mechanism of death was unknown, real-time imaging was employed for cells in a 5% $CO_2$ and temperature-regulated (37° C.) chamber to monitor the effects of JC21mLHRH and JCHmLHRH on PC-3 cellular responses. There were morphological changes in cells exposed to either JC21mLHRH or JCHmLHRH for 3 h.

Figure 5A:
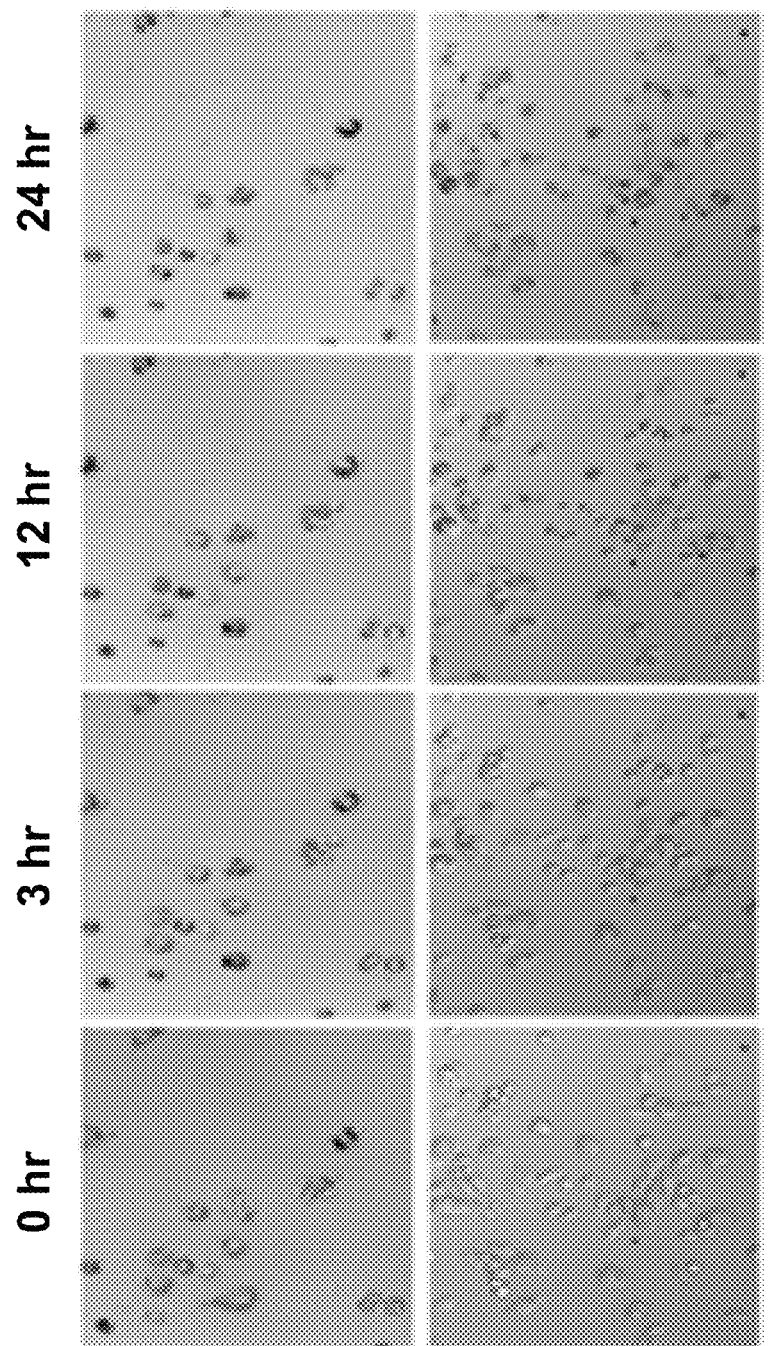
FIG. 5A is a table displaying eight black and white photographs that are real-time images of representative samples of PC-3 cells after treatment with lytic peptides JCHmLHRH (5 μM) or JC21mLHRH (8 μM) taken with time-lapse microscopy under 5% $CO_2$ and 37° C. at 0, 3, 6, and 12 hours post administration.

PC-3 cell cultures were exposed to JCHmLHRH (5 µM) or JC21mLHRH (8 µM) and imaged continuously for 24 h with time-lapse microscopy. FIG. 5A comprises eight black and white photographs depicting real-time images of PC-3 cells after treatment with lytic peptides JCHmLHRH (5 µM) or JC21mLHRH (8 µM) taken with time-lapse microscopy under 5% $CO_2$ and 37° C. at 0, 3, 6, and 12 hours post administration. JCHmLHRH was observed under microscope to cause membrane rupture and cell bursting; while cells exposed to JC21mLHRH showed a condensing of the cellular and nuclear membrane without bursting. There were different modes of action by which JCHmLHRH and JC21mLHRH caused cell death. Exposure to JCHmLHRH resulted in shrinkage and eventual bursting of the cell membrane. While cells exposed to JC21mLHRH showed a condensing of the cellular and nuclear membranes, but did not burst.

Figure 5B:
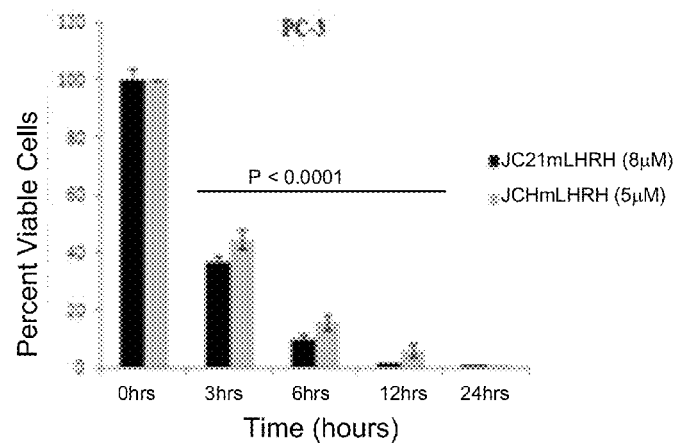
FIG. 5B is a graph reporting experimental results for cell percentage corresponding to the images of FIG. 5A.

FIG. 5B is a graph reporting experimental results for cell percentage corresponding to the images of FIG. 5A. Quantification of total cell number and cell viability was determined by trypan blue exclusion after exposure to JCHmLHRH (5 µM) or JC21mLHRH (8 µM) over a 24 h period. The results shown in the graph of FIG. 5B are representative of three individual experiments performed in triplicate (where the horizontal line at approximately 60% in the graph indicates significance at $p<0.0001$). The data indicates a rapid mode of action was observed by both the real-time imaging and trypan blue staining mechanisms, with nearly 80% cell death after only 6 h of treatment and approximately 100% cell death after the 24 h period. As determined by trypan blue exclusion assay, a significant increase in cell death ($p<0.001$) was observed at 3 h and 6 h time periods for both peptides. Additionally, tests of the exposed cells did not observe expression of apoptotic marker Annexin V. These results are consistent with other previous reports utilizing lytic peptides in cancer studies that suggest necrosis as the main mode of action rather than apoptosis (see, for example, Bodek G, Kowalczyk A, Waclawik A, Huhtaniemi I, Ziecik A J; Targeted ablation of prostate carcinoma cells through LH receptor using Hecate-CGbeta conjugate: functional characteristic and molecular mechanism of cell death pathway; Exp Biol Med (Maywood); 2005; 230:421-8).

Regardless of the mechanism of action, both peptides appeared to cause significant tumor-specific cell death. Tumor cell specificity was evident from the finding that neither peptide had an appreciable anti-proliferative effect on either non-cancerous hPrEC cells or highly proliferative HS-27a bone stromal cells in PC-3/HS-27a co-cultures (see FIG. 5C, FIG. 5D, and FIG. 5E). This data supports that the peptides will have potentially limited cytotoxic effects on the surrounding stroma of cancer cells located at primary and metastatic sites in vivo. Further, the effect of exposure to these mLHRH-conjugated peptides was sufficient to inhibit the growth of PC-3 cells up to 3 days in the absence of the lytic peptide (see FIG. 6). Whether the lack of PC-3 growth after LHRH-conjugated peptide pretreatment was due to a loss of cells or to the prevention of cellular proliferation was not determined. The net result, however, is that both peptide sequences were effective in inhibiting cell growth. A possible mechanism for the differential effect of JCHmLHRH compared to JC21mLHRH may be their direct interaction with the cancer cell membrane, and it is possible that the peptide sequence determines the type of membrane-mediated cell death.

Example 6

This experiment utilizes a three-dimensional method of utilizing bone marrow stromal cells and prostate cancer cell line co-cultures to delineate the influence of the host stromal cells on metastatic prostate cancer cells (see Josson S, Sharp S, Aneja R, Wang R, Turner T, Chung L, et al., Tumor-stromal interactions influence radiation sensitivity in epithelial—versus mesenchymal-like prostate cancer cells, J Onocol 2010; 2010:10), which method has been shown to reproducibly mimic the in vivo situation. This method may be used to demonstrate the tumor targeting specificity of peptides for metastatic prostate cancer by utilizing cultures and co-cultures of GFP-HS-27a bone marrow stromal cells and PC-3 cells.

For this experiment, RFP-PC-3 cell cultures, GFP-HS-27a cell cultures, and RFP-PC-3/GFP-HS-27a cell co-cultures were exposed to JCHmLHRH (5 µM) and JC21mLHRH (8 µM), and the various cultures were monitored by differential immunofluorescence over 12 h period. Images comprising black and white photographs of the cultures at the 0 hr, 6 hr, and 12 hr marks following administration of JCHmLHRH and JC21mLHRH are shown in FIG. 5C and FIG. 5D, respectively. Two trials of this experiment were conducted with similar results, and the photographs of FIG. 5C and FIG. 5D are illustrative of the results of both trials. As can be deduced by visual comparison of the photographs, for both peptides the total number of cells in the RFP-PC-3 cultures decreases quickly and significantly over the 12 hr period, while the images for the GFP-HS-27a cultures remains largely unchanged over the 12 hr period. Further, the RFP-PC-3/GFP-HS-27a co-culture images at the 6 hr and 12 hr marks largely resemble the corresponding time images for GFP-HS-27a cultures in relative intensity.

Figure 5E:
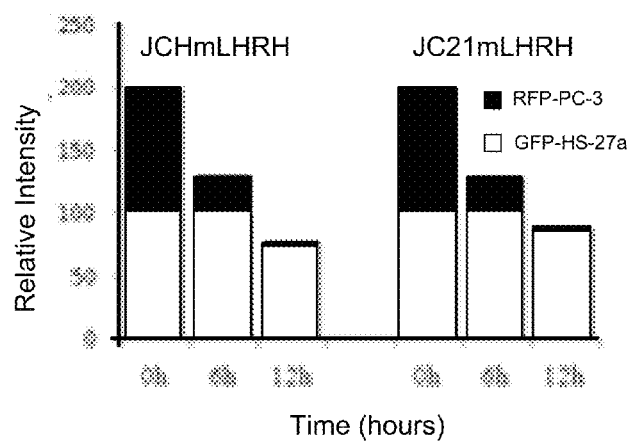
FIG. 5E is a graph reporting experimental results for the relative intensity for the differential immunofluorescence experiments underlying FIG. 5C and FIG. 5D, with each bar of the graph of FIG. 5E representing n=4 images sectioned and individually analyzed for total area.
Figure 5C:
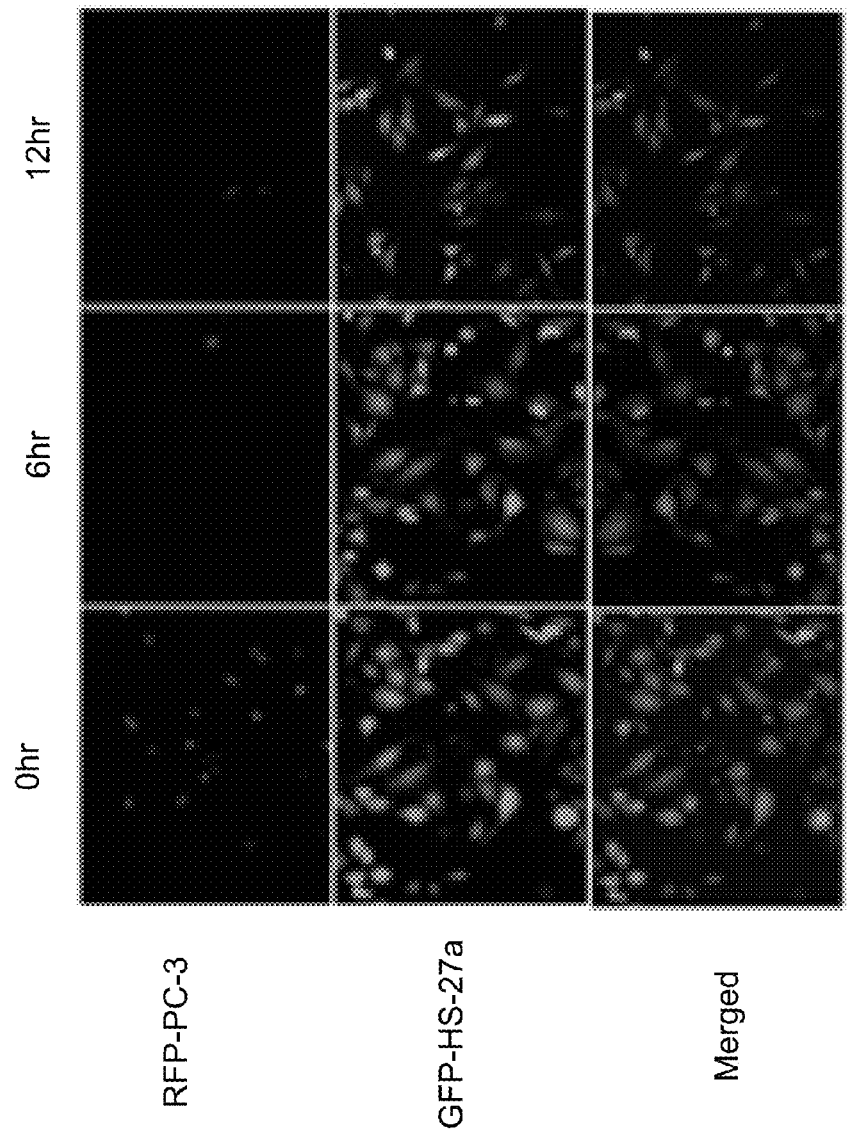
FIG. 5C and FIG. 5D are tables displaying color photographs (nine each) depicting differential immuno-fluorescence of RFP-PC-3 cell cultures, GFP-HS-27a cell cultures, and RFP-PC-3/GFP-HS-27a co-cultures after treatment with lytic peptides JCHmLHRH (5 μM) or JC21mLHRH (8 μM) taken at 0, 6, and 12 hours post administration.
Figure 5D:
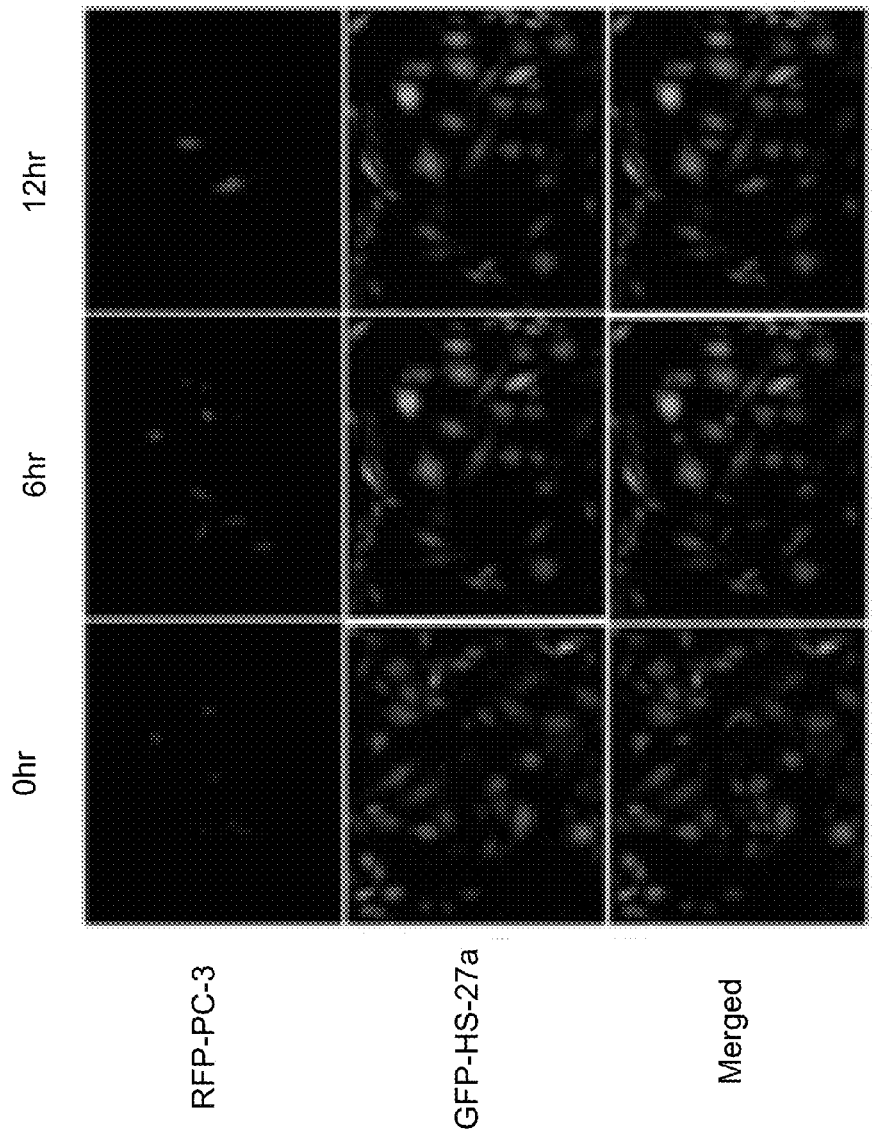
Figure 6:
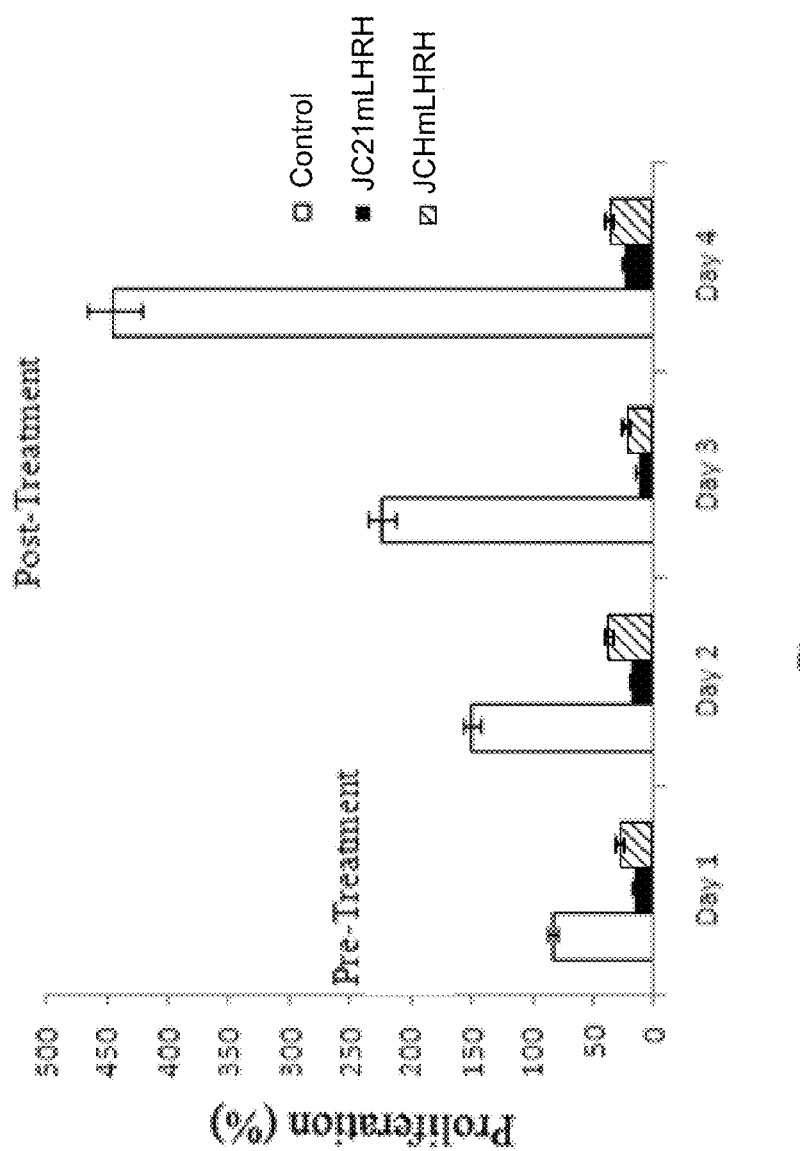
FIG. 6 is a graph illustrating experimental results for growth of PC-3 cells over a 3-day period following pretreatment with JCHmLHRH (5 μM) or JC21mLHRH (8 μM) for 24 hrs (with bars representing the mean number of cells survived.

FIG. 5E in turn provides a chart showing the relative intensity of total areas measured under differential fluorescence of the co-culture cells after they were exposed to JCHmLHRH and JC21mLHRH in this experiment. As can be seen, for this experiment the relative intensity of the RFP-PC-3 cells decreases quickly and approaches zero at the 12 hr mark, while the relative intensity of the GFP-HS-27a cells only decreases slightly. The differential fluorescence data demonstrates that, in the presence of either peptide, there was appreciable death of PC-3 cells in 12 hour, but little effect was observed on GFP-HS-27a cells. These results indicate that the peptides had strong lytic action in the co-cultures against the cancer cells without significant toxicity to the non-cancerous cells, making it likely that the peptides when administered as a medicament would in vivo target and kill (or inhibit the proliferation of) cancerous cells without unwanted toxicity to non-cancerous cells.

Example 7

This experiment was performed to determine whether cancerous cells could recover after JCHmLHRH or JC21mLHRH exposure. PC-3 cell cultures were exposed to JCHmLHRH (5 μM) or JC21mLHRH (8 μM) for 24 hours. Growth was measured over a 3-day period. Growth of pre-treatment and post-treatment groups were compared over time. As shown in the graph of FIG. 5 (bars representing the mean number of cells survived as determined by MIT, Mean±s.d. (n=4), *p<0.005, Student's t-test), pretreatment completely inhibited cell growth over the 3 days assayed, while there was no significant differences observed between pre- and post-treatment.

Because current data suggests that LHRH-Rs are expressed in 86% of human prostate cancers and LHRH-R numbers increase with the increasing metastatic potential of prostate cancer cell lines, it is reasonable to expect that the above in vitro findings will translate in vivo and ultimately have clinical utility in humans. Additionally, given that the low concentration and unique mode of action the peptides disclosed herein differ from other classical chemotherapeutic agents, one can extrapolate that the combined use of these conjugated peptides with similar agents or within nanotechnology-directed therapies should enhance their therapeutic values and limit toxicity to non-tumor cells. Thus, it is well within the skill of one of ordinary skill in the art to conduct animal cancer model studies to confirm the efficacy and non-toxicity of the lytic peptides and conjugates disclosed herein and identify suitable dosage and therapeutic delivery forms for ultimate use in the treatment of local and metastatic prostate cancer.

Thus, the various experiments and accompanying results summarized above provide evidence that peptides JCH and JC21 inhibit cancer cell proliferation at low concentrations, and, when conjugated with the mLHRH sequence, both peptides have enhanced anti-proliferative activity. The experimental results demonstrate that both JCHmLHRH and JC21mLHRH destroy LNCaP, DU-145, and PC-3 prostate cancer cells. Thus, JCH and JC21, whether or not conjugated with mLHRH, were identified as new therapies for prostate cancer. Furthermore, peptides JCHmLHRH and JC21mLHRH demonstrate minimal anti-proliferative effects on normal prostate cells, even at relatively high concentrations. Real-time imaging reveals that these specific peptides cause morphological changes in PC-3 cells after 3 h of exposure, and exert toxicity in PC-3 cells within 6 h of exposure (potentially through different modes of action), while pre-treatment of PC-3 cells with these peptides blocks their growth over a 3-day period. The experimental results indicate that human prostate cancer cell lines were sensitive to both mLHRH-conjugated and non-conjugated lytic peptides, with $IC_{50}$ concentrations for LNCaP cells, 4.4 and 9.1 μM; for DU-145 cells, 4.8 and 5.7 μM; and for PC-3 cells, 4.4 and 8.2 μM, respectively. JCHmLHRH and JC21mLHRH were non-toxic to normal primary human prostate epithelial cells or to bone marrow stromal cells in co-culture. Since JCHmLHRH and JC21mLHRH have specificity for and anti-proliferative activity against tumor cells, and low toxicity for normal prostate cells, these peptides were identified as new compounds that may be used in therapies for treating prostate cancer according to preferred embodiments of the invention, including hormone-refractory prostate cancer.

The findings reported herein parallel those from previously reported lytic-LHRH conjugated peptides, where a lytic sequence alone was less effective in decreasing proliferation when compared to conjugates of the sequence with unmodified LHRH. A major difference, however, between findings above from prior reported lytic peptides is that the prior reported peptides required circulating estradiol or follicle-stimulating hormone to be active. Previous studies utilizing lytic peptides have highlighted the importance of a steroid presence, since the removal of steroids from the culture media eliminated the sensitivity of prostate cancer cells to the effects of lytic-LHRH conjugates. The lytic peptides of the present invention do not require this, as evidenced by the fact that all culture experiments in the Examples above were performed with serum-free media. Furthermore, the lytic peptides without conjugated LHRH showed substantial activity and selectivity for prostate cancer cells. Thus, it appears that these peptides act directly on the membrane, with the LHRH sequence increasing activity and enhancing selectivity.

Having described preferred embodiments of the invention, it will now become apparent to those of ordinary skill in the art that other embodiments incorporating these concepts may be used. Accordingly, it is submitted that that the invention should not be limited to the described embodiments but rather should be limited only by the spirit and scope of the appended claims.

Thus, although the invention has been described and illustrated with a certain degree of particularity, it is understood that the present disclosure has been made only by way of example, and that numerous changes in the combination and arrangement of steps, ingredients, or processes can be resorted to by those skilled in the art without departing from the spirit and scope of the invention, as will be claimed.

| BIOSEQUENCES |
|---|
| SEQ. ID NO. 1-JCH<br>FALALKALKKALKKLKKLKKALKKAL |
| SEQ. ID NO.: 2-JC21<br>AFKKAFKKAKKAFKKAFKAFAFA |
| SEQ. ID NO.: 3-LHRH<br>QHWSYGLRPG |

| BIOSEQUENCES |
|---|
| SEQ. ID NO.: 4-mLHRH<br>QHWSWGLRPG |
| SEQ. ID NO.: 5-JCHmLHRH<br>QHWSWGLRPGFALALKALKKALKKLKKALKKAL |
| SEQ. ID NO.: 6-JC21mLHRH<br>QHWSWGLRPGAFKKAFKKAKKAFKKAFKAFAFA |

| BIOSEQUENCES |
|---|
| SEQ. ID NO.: 7-JCHLHRH<br>QHWSYGLRPGFALALKALKKALKKLKKALKKAL |
| SEQ. ID NO.: 8-JC21LHRH<br>QHWSYGLRPGAFKKAFKKAKKAFKKAFKAFAFA |

The invention claimed is:

1. A compound comprising a peptide having first domain and a second domain, wherein: (a) said first domain comprises a modified luteinizing hormone-releasing hormone ("mLHRH") having the sequence SEQ ID NO: 4, and (b) said second domain comprises a lytic peptide, wherein said lytic peptide has the sequence SEQ ID NO:1 and has anti-proliferative activity against tumor cells that express elevated levels of luteinizing hormone-releasing hormone receptor ("LHRH-R").

2. The compound according to claim 1, wherein said lytic peptide causes shrinkage of cell membrane of said tumor cells.

3. The compound according to claim 1, wherein said compound comprises the sequence SEQ ID NO: 5.

4. A pharmaceutical product comprising a pharmaceutically effective amount of the compound as recited in claim 1 in a pharmaceutically acceptable solvent.

5. A method for inhibiting prostate tumor cell proliferation in a mammal, in need thereof comprising administering to the mammal an effective amount of the compound as recited in claim 1.

6. The method as recited in claim 5, wherein said compound comprises vitamin B12 linked to said peptide.

7. A method for inhibiting proliferation of tumor cells in a mammal where said tumor cells express elevated levels of LHRH-R, said method comprising administering to the mammal an effective amount of the compound as recited in claim 1.

8. The method as recited in claim 7, wherein said mammal is diagnosed as having a prostate cancer tumor.

9. The method as recited in claim 7, wherein said compound further comprises a third domain, and wherein said third domain comprises a type selected from the group consisting of carrier to facilitate uptake by the intestine when the compound is administered orally to said mammal, and a linking domain.

10. The method as recited in claim 9, wherein said second compound further comprises vitamin B12 bound to said peptide.

* * * * *